United States Patent
Huang (10) Patent No.: US 10,470,896 B2
(45) Date of Patent: Nov. 12, 2019

(54) SURGICAL INSERTER

(71) Applicant: Ren-Hong Huang, Miaoli County (TW)

(72) Inventor: Ren-Hong Huang, Miaoli County (TW)

( * ) Notice: Subject to any disclaimer, the term of this patent is extended or adjusted under 35 U.S.C. 154(b) by 476 days.

(21) Appl. No.: 15/219,212

(22) Filed: Jul. 25, 2016

(65) Prior Publication Data

US 2017/0027715 A1 Feb. 2, 2017

Related U.S. Application Data

(60) Provisional application No. 62/197,521, filed on Jul. 27, 2015.

(51) Int. Cl.
| | | |
|---|---|---|
| *A61F 2/46* | (2006.01) | |
| *A61B 17/88* | (2006.01) | |
| *A61F 2/34* | (2006.01) | |
| *A61B 17/00* | (2006.01) | |

(52) U.S. Cl.
CPC ........ *A61F 2/4609* (2013.01); *A61B 17/8872* (2013.01); *A61F 2/34* (2013.01); *A61F 2/4684* (2013.01); *A61B 2017/00407* (2013.01); *A61B 2017/00464* (2013.01); *A61B 2017/00469* (2013.01); *A61F 2002/4624* (2013.01); *A61F 2002/4629* (2013.01)

(58) Field of Classification Search
CPC .. A61F 2/4609; A61F 2/46; A61F 2002/4624; A61F 2002/4629
See application file for complete search history.

(56) References Cited

U.S. PATENT DOCUMENTS

| | | | | |
|---|---|---|---|---|
| 6,626,913 B1* | 9/2003 | McKinnon | ............... | A61F 2/367 606/86 R |
| 2007/0167952 A1* | 7/2007 | Burgi | .................... | A61B 17/162 606/99 |
| 2007/0173856 A1* | 7/2007 | Parker | ....................... | A61F 2/34 606/99 |
| 2009/0192515 A1* | 7/2009 | Lechot | .................. | A61F 2/4609 606/91 |
| 2010/0318192 A1* | 12/2010 | Laffay | ....................... | A61F 2/34 623/22.21 |
| 2012/0184965 A1* | 7/2012 | Burgi | .................... | A61F 2/4609 606/99 |
| 2013/0079785 A1* | 3/2013 | Burgi | .................... | A61F 2/4609 606/91 |
| 2013/0226186 A1* | 8/2013 | Burgi | ..................... | A61B 17/56 606/91 |
| 2014/0081283 A1* | 3/2014 | Liang | .................... | A61F 2/4609 606/99 |

(Continued)

*Primary Examiner* — David W Bates
(74) *Attorney, Agent, or Firm* — Winston Hsu (57) ABSTRACT

A surgical inserter includes a shaft, a lever, a bolt, and a locking mechanism. The shaft includes a shaft body and an engaging head. An end of the lever is adjacent to an inner side of the engaging head. The bolt is mounted on the end of the lever and passes through the engaging head to connect a medical device. The locking mechanism is movably disposed on the other end of the shaft body for selectively locking or releasing angular movement of the lever relative to the shaft body. When the lever is bending relative to the shaft body, the end of the lever pries the bolt, so that the medical device is driven by the bolt to abut against an outer side of the engaging head tightly.

19 Claims, 14 Drawing Sheets

(56) References Cited

U.S. PATENT DOCUMENTS

| | | | |
|---|---|---|---|
| 2014/0276838 A1* | 9/2014 | Tsukayama | A61B 17/1675 606/80 |
| 2016/0100956 A1* | 4/2016 | Conley | A61F 2/4609 606/91 |
| 2016/0135963 A1* | 5/2016 | Kerboul | A61F 2/4609 606/91 |
| 2016/0213492 A1* | 7/2016 | Castello | A61F 2/4609 |
| 2017/0304078 A1* | 10/2017 | Chenaux | A61F 2/34 |
| 2018/0014948 A1* | 1/2018 | Bonin | A61F 2/4609 |
| 2018/0280157 A1* | 10/2018 | Schmit | A61F 2/4609 |

* cited by examiner

SURGICAL INSERTER

CROSS REFERENCE TO RELATED APPLICATIONS

This application claims the benefit of U.S. Provisional Patent Application No. 62/197,521 filed on Jul. 27, 2015, which is hereby incorporated by reference in its entirety.

BACKGROUND OF THE INVENTION

1. Field of the Invention

The present invention relates to a surgical inserter for a medical device, and more particularly, to a surgical inserter, which is capable of being connected to a medical device firmly and being cleaned easily.

2. Description of the Prior Art

During a surgery, a medical device, such as a prosthetic implant, a provisional implant or an instrument, is usually connected with a tool for easy operation. In order to prevent a releasable connection between the medical device and the tool from getting loosen during operation, an auxiliary mechanism is usually used for fastening the medical device and the tool.

However, the auxiliary mechanism usually includes complicated linkages, multiple joints, small parts, deep channels, deep undercuts, and etc., which increases difficulty of cleaning and sterilization. In a surgical application, components contact with blood, tissue fragments, and bone chips frequently. Therefore, complex designs substantially increase a risk of infection.

In order to solve the problem of infection, there are some surgical tools designed to be partially disassembled for cleaning and sterilization. However, complex structure is still not reliable, which may cause delay in surgery. Furthermore, complicated cleaning procedure of the conventional surgical tools increases medical staff's burden and hospital operating costs.

SUMMARY OF THE INVENTION

Therefore, an objective of the present invention is to provide a surgical inserter, which is capable of being connected to a medical device firmly and being cleaned easily, for solving the aforementioned drawbacks.

The present embodiment utilizes a lever for prying a bolt to drive a medical device to abut against an outer side of an engaging head tightly. The embodiment further utilizes a locking mechanism for locking angular movement of the bending lever relative to a shaft body, so as to ensure the medical device to be securing all the times. Therefore, the embodiment prevents loose movement of the medical device relative to the surgical inserter during a surgical operation, which is more reliable and enhances precision of surgical operation. Besides, since structure of the surgical inserter of the present embodiment is simpler than conventional designs, the present embodiment has advantages of convenient operation and easy cleaning and sterilization. Therefore, the surgical inserter of the present embodiment can substantially relief medical staff's burden and reduces a risk of infection.

DETAILED DESCRIPTION

In order to illustrate technical specifications and structural features as well as achieved purposes and effects of the present invention, relevant embodiments and figures are described as follows.

Figure 1:
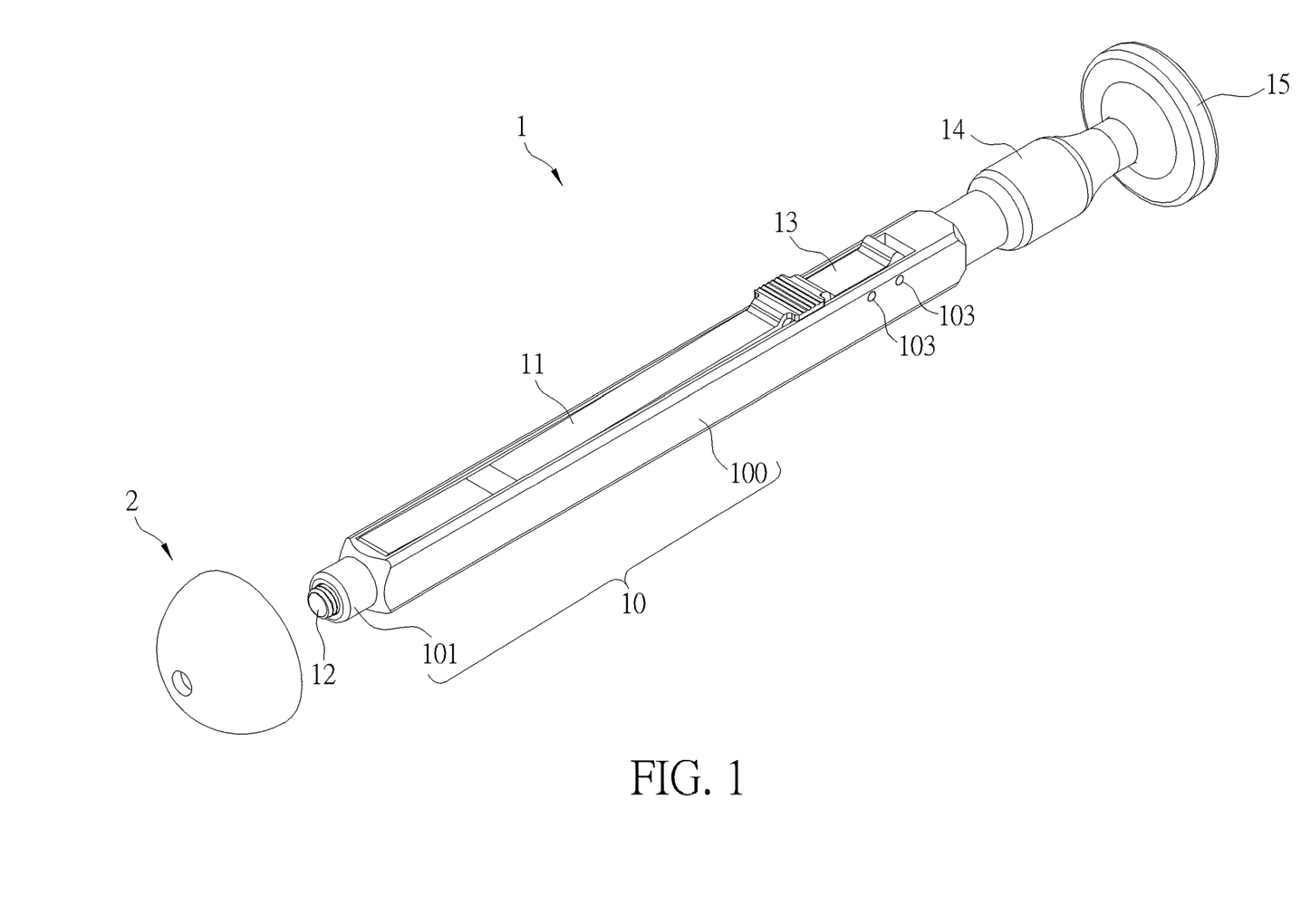
FIG. 1 is a schematic diagram of a surgical inserter according to a first embodiment.
Figure 2:
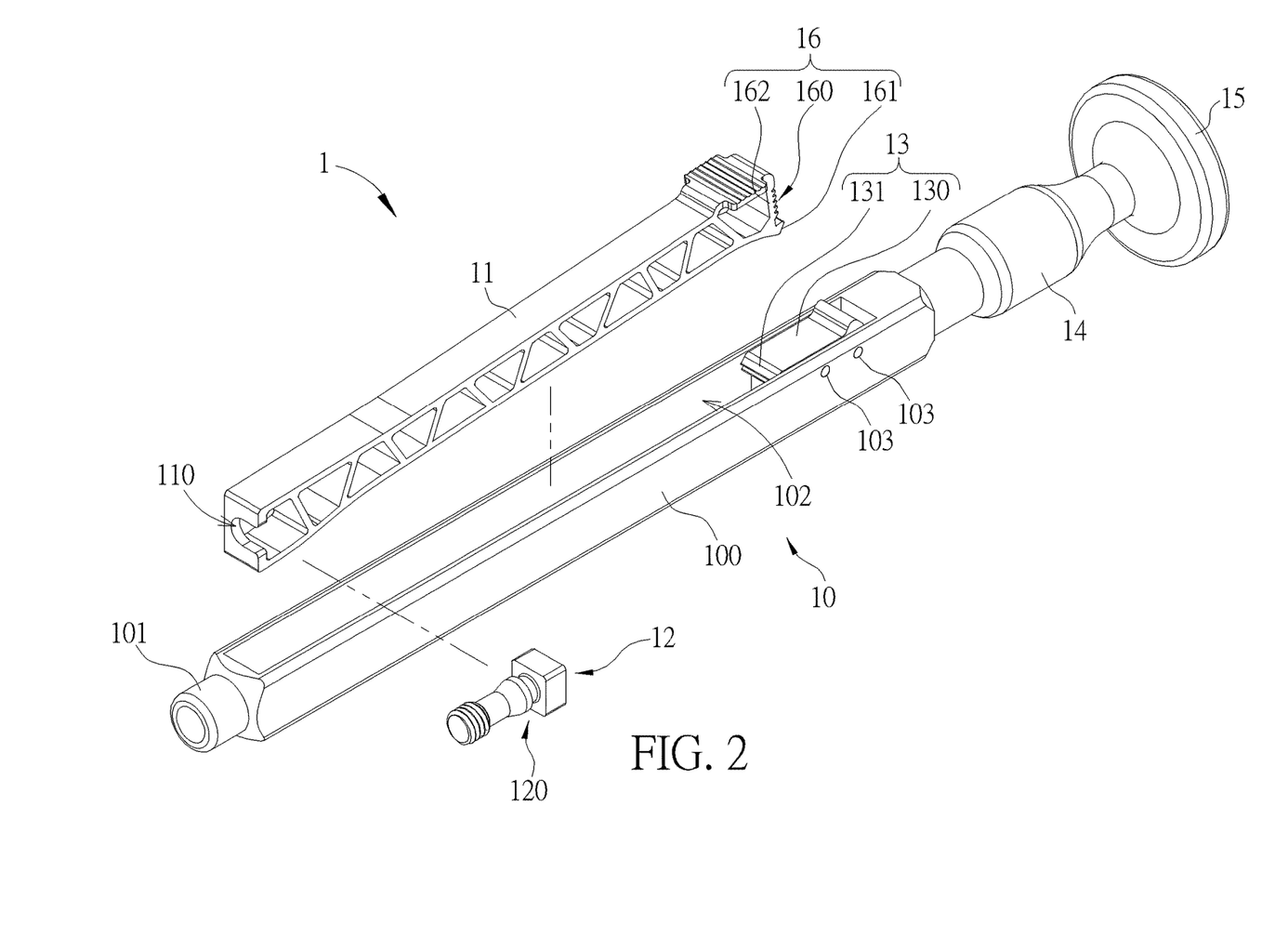
FIG. 2 is an exploded diagram of the surgical inserter according to the first embodiment.

Please refer to FIGS. 1 and 2. A surgical inserter 1 is for connecting a medical device 2. The inserter 1 includes a shaft 10, a lever 11, a bolt 12, a locking mechanism 13, a handle portion 14, and an impaction plate 15. The shaft 10 includes a shaft body 100 and an engaging head 101. The engaging head 101 is disposed on an end of shaft body 100. The lever 11 is movably disposed on shaft body 100. An end of lever 11 is adjacent to an inner side of engaging head 101. Bolt 12 is mounted on the end of lever 11 and passes through engaging head 101 to connect device 2. The locking mechanism 13 is movably disposed on the other end of shaft body 100 away from engaging head 101. The locking mechanism 13 selectively locks or releases angular movement of lever 11 relative to shaft body 100. In this embodiment, an accommodating slot 102 is formed on a side of shaft body 100 for receiving lever 11 and locking mechanism 13. The lever 11 is detachably disposed in slot 102. However, in another embodiment, lever 11 and shaft body 100 also can be disposed side by side. The handle 14 extends from the other end of shaft body 100. The plate 15 is connected to handle 14 for receiving an external force. The handle 14 and plate 15 allow a user to manipulate and apply force for the insertion of device 2. For example, in this embodiment, the inserter 1 can be an acetabular cup inserter, and the device 2 can be an acetabular cup implant. However, the inserter 1 also can be connected to another device other than the acetabular cup implant.

In this embodiment, the inserter 1 further includes a first ratchet 16 disposed on the other end of lever 11. The locking mechanism 13 includes a locking body 130 and a second ratchet 131. The locking body 130 is slidably connected to shaft body 100. For example, the locking body 130 can be slidably connected to shaft body 100 by cooperation of pins and slots. The second ratchet 131 is disposed on a side of locking body 130 corresponding to first ratchet 16. The first ratchet 16 can selectively engage and disengage with second ratchet 131 for locking or releasing the angular movement of lever 11 relative to the shaft body 100. However, in another embodiment, first ratchet 16 and second ratchet 131 can be replaced by other components, such as cams, eccentrics, or gear wheels.

Furthermore, first ratchet 16 includes a plurality of first teeth 160, a first engaging hook 161, and a first ratchet body 162. The first teeth 160 and first engaging hook 161 protrude from first ratchet body 162. The first engaging hook 161 is located at a side of first teeth 160. A height of each first tooth 160 is less than a height of first engaging hook 161.

Figure 3:
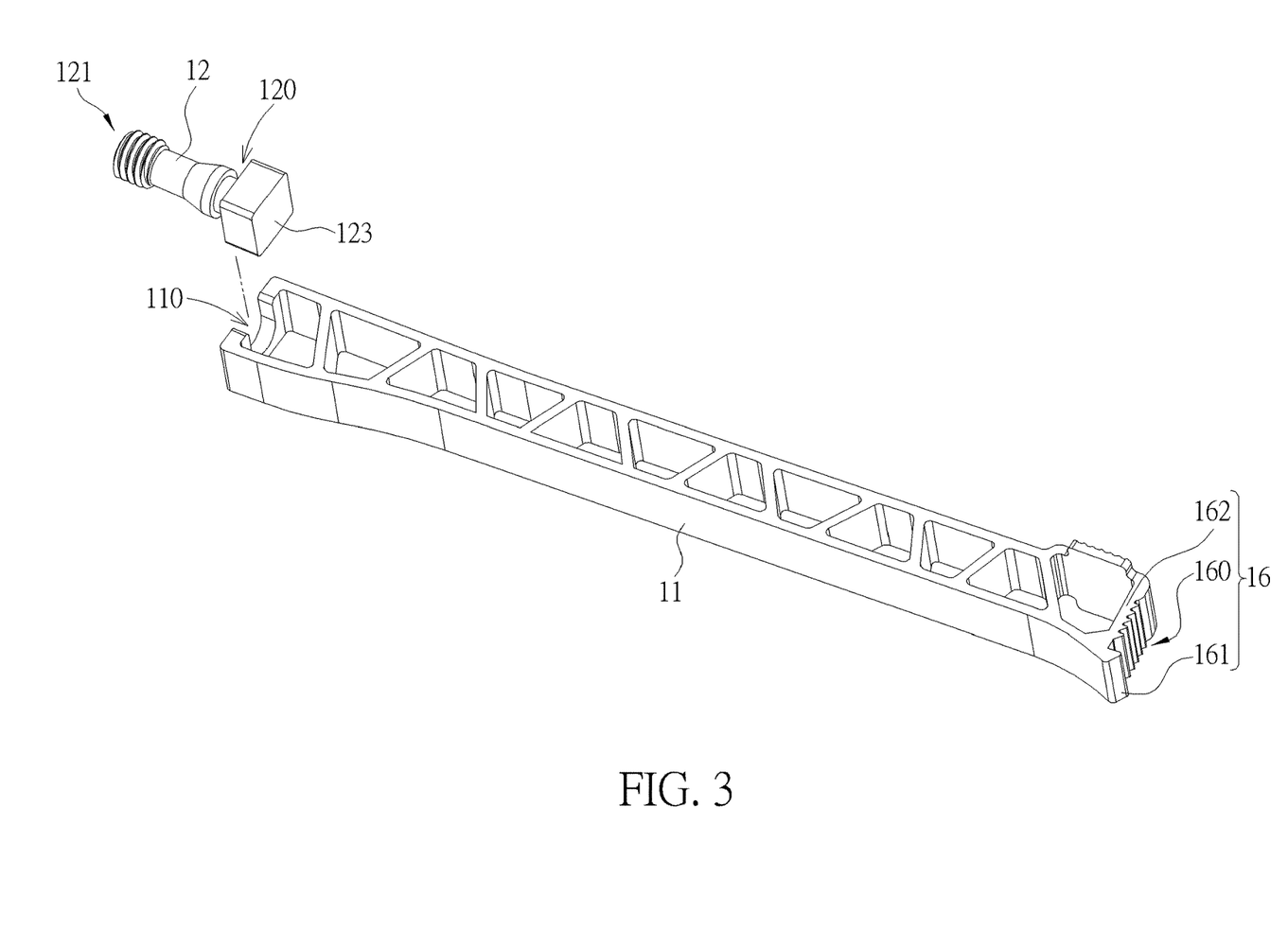
FIG. 3 is a diagram of a lever and a bolt according to the first embodiment.
Figure 4:
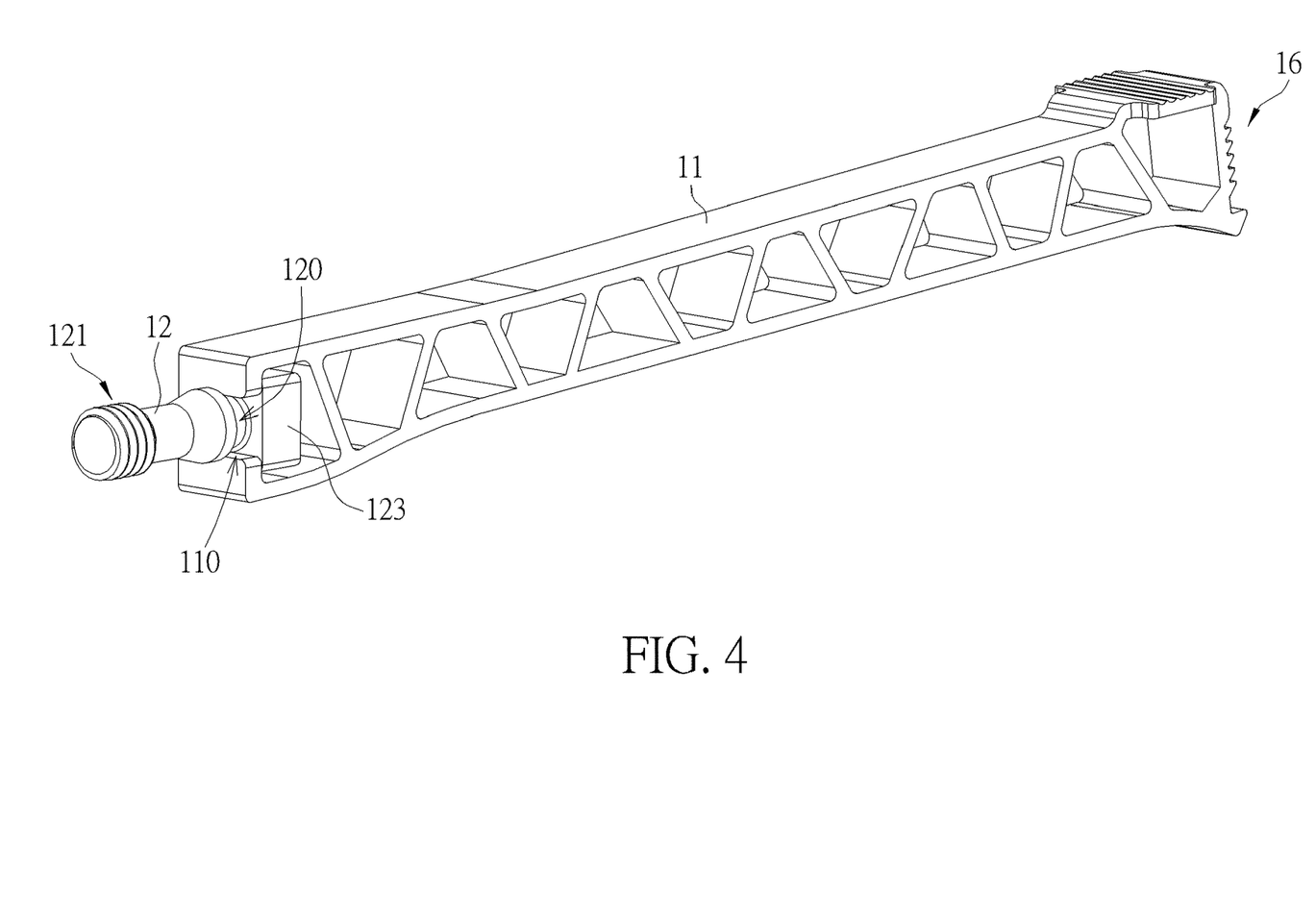
FIG. 4 is another diagram of the lever and the bolt according to the first embodiment.

Please refer to FIGS. 2 to 4. In this embodiment, each of shaft body 100 and lever 11 is formed in a straight shape, and a head 123 of bolt 12 is received in lever 11 and rotated along with shaft body 100 and lever 11. A notch 110 is formed on the end of lever 11 near engaging head 101. The bolt 12 includes a neck portion 120 for engaging with notch 110 on lever 11 and a connecting portion 121 for connecting device 2. In this embodiment, the connecting portion 121 is connected to the device 2 by a threaded connection. However, in another embodiment, the connecting portion 121 also can be a bayonet connection or a dovetail connection.

Figure 5:
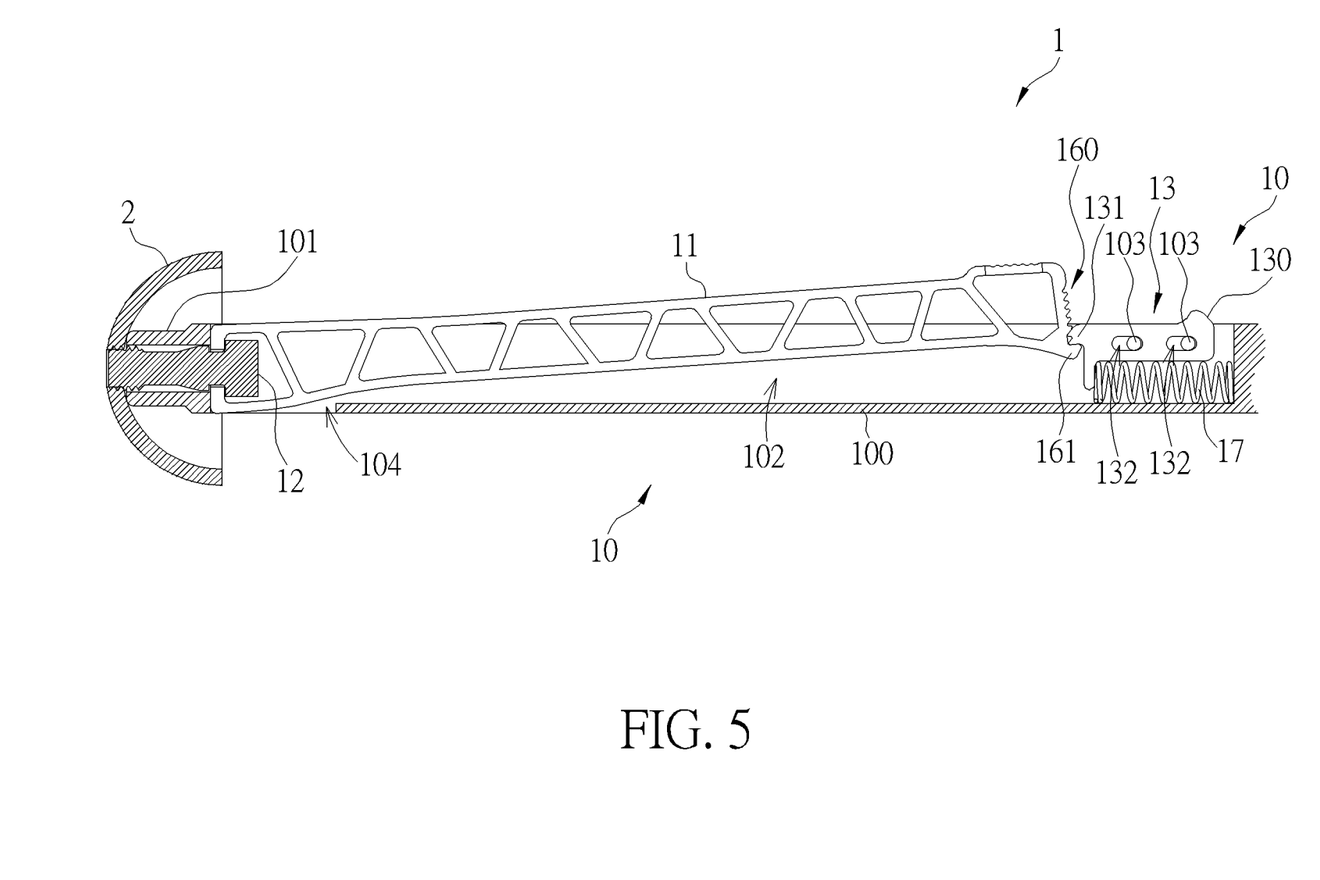
FIG. 5 is a diagram of the surgical inserter at an unlocking status according to the first embodiment.
Figure 6:
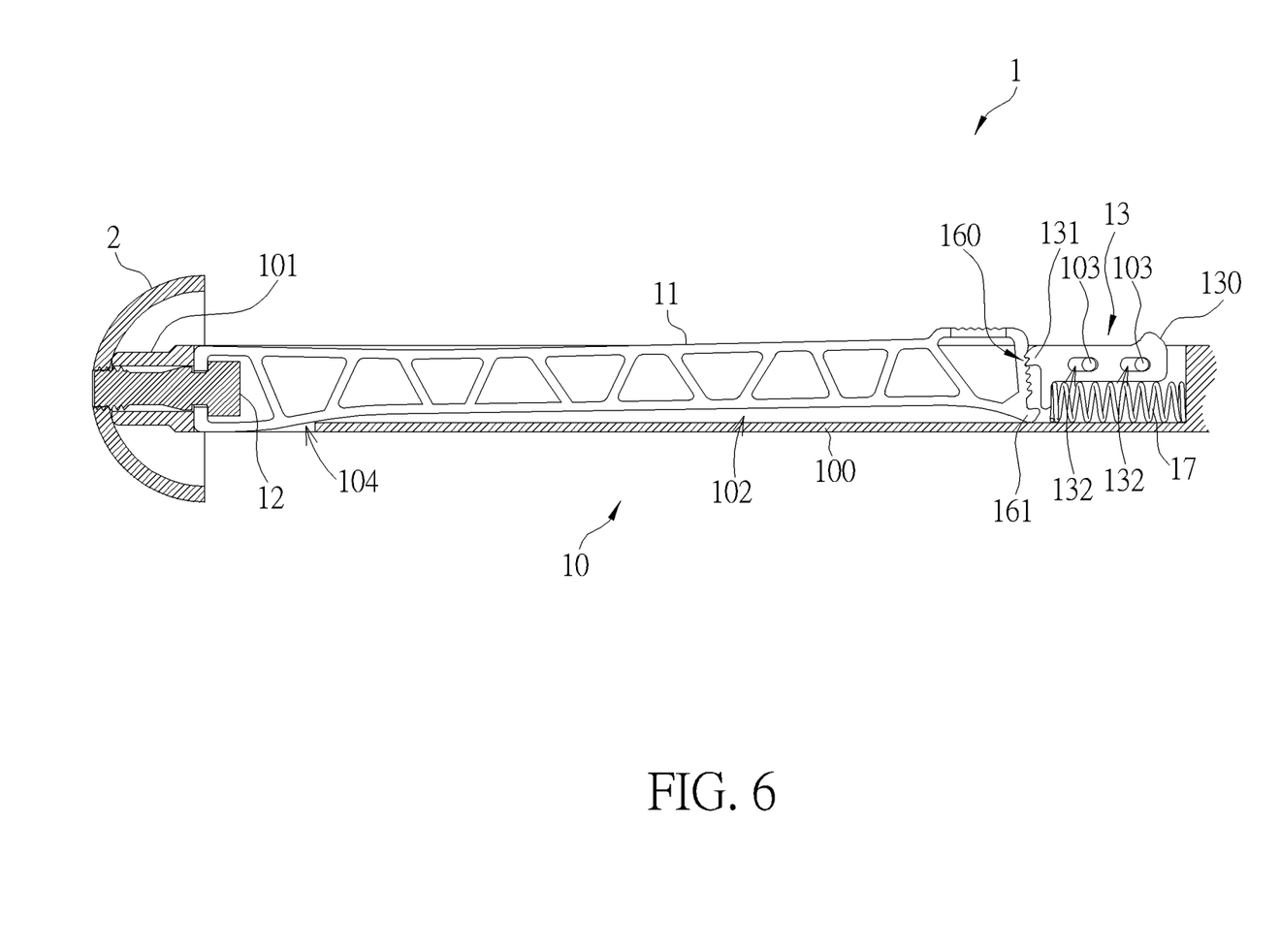
FIG. 6 is a diagram of the surgical inserter at a locking status according to the first embodiment.
Figure 7:
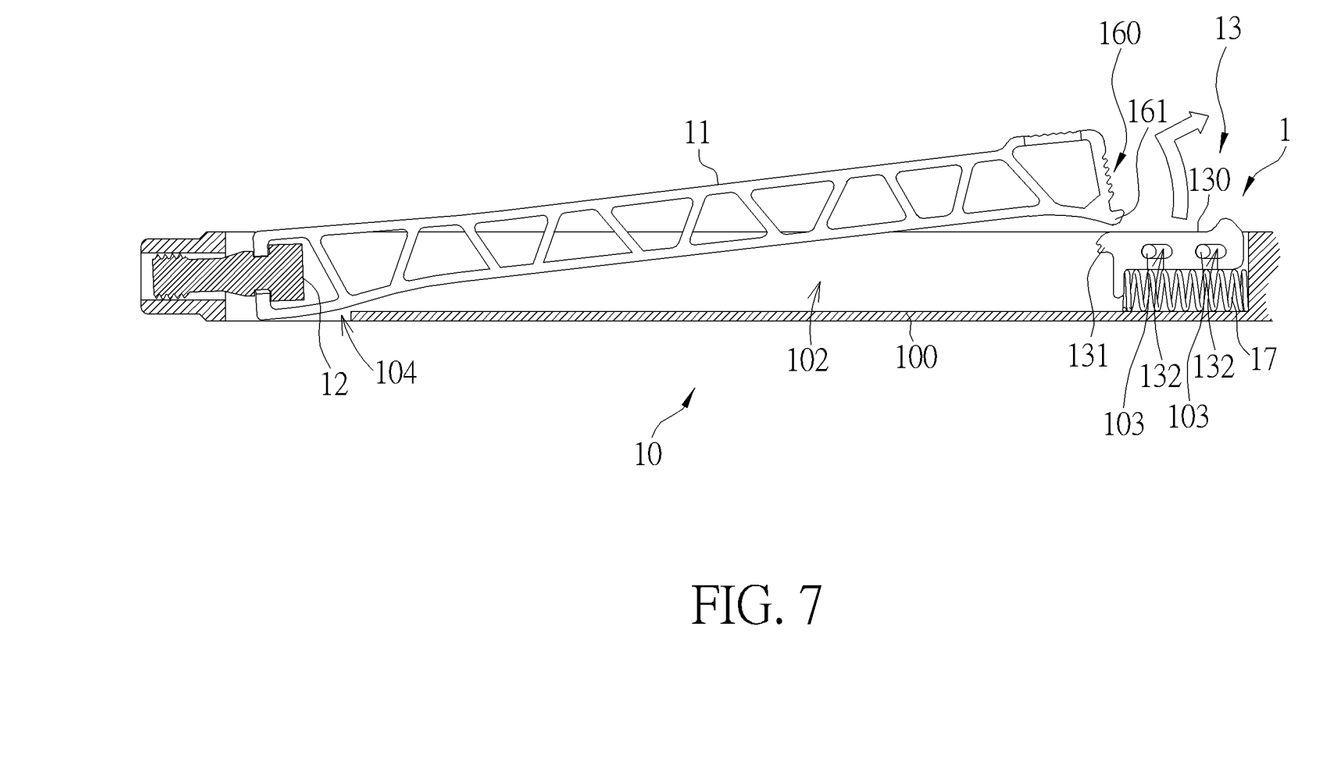
FIG. 7 is a diagram of the surgical inserter at a disassembling status according to the first embodiment.
Figure 8:
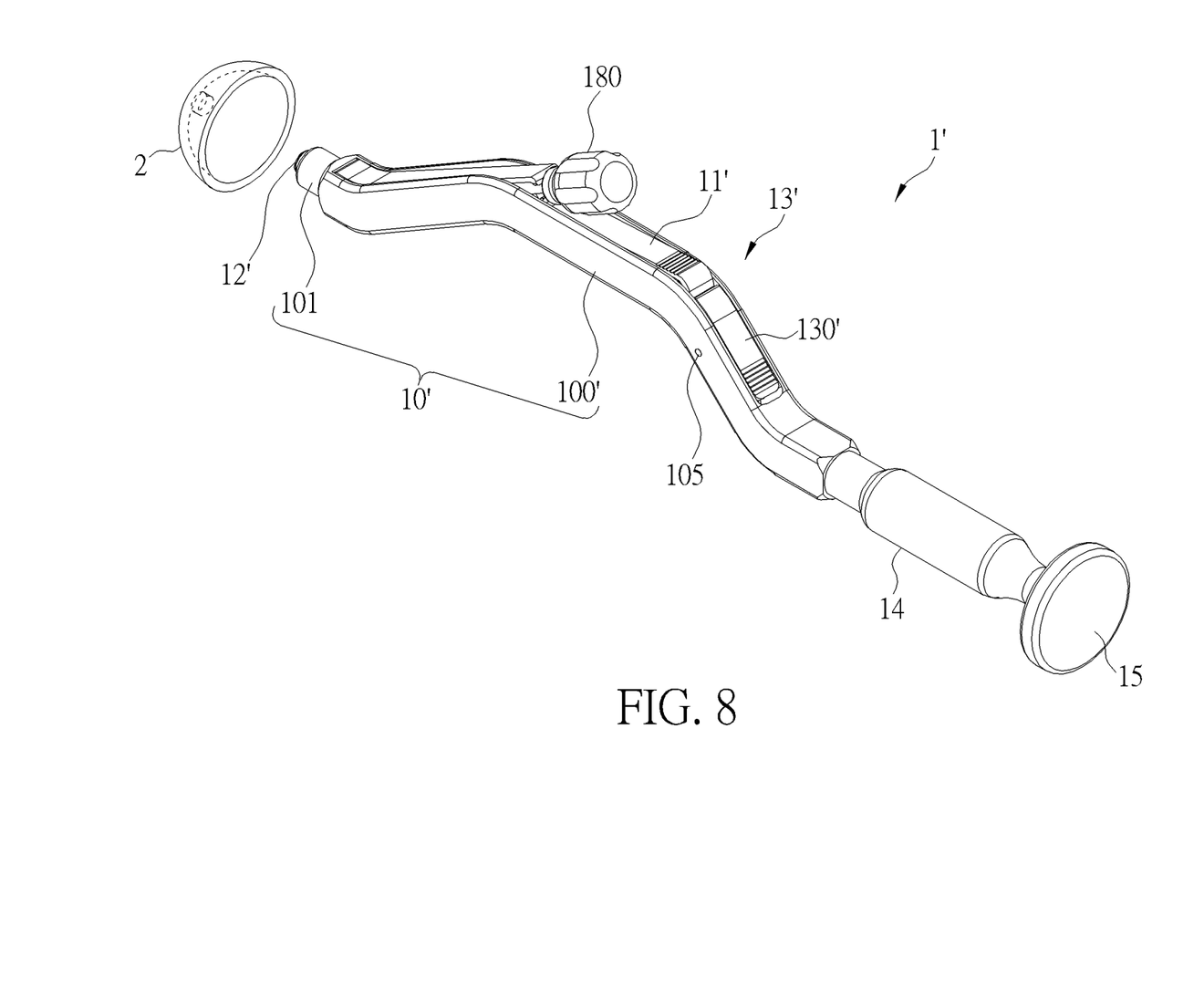
FIG. 8 is a schematic diagram of a surgical inserter according to a second embodiment.
Figure 9:
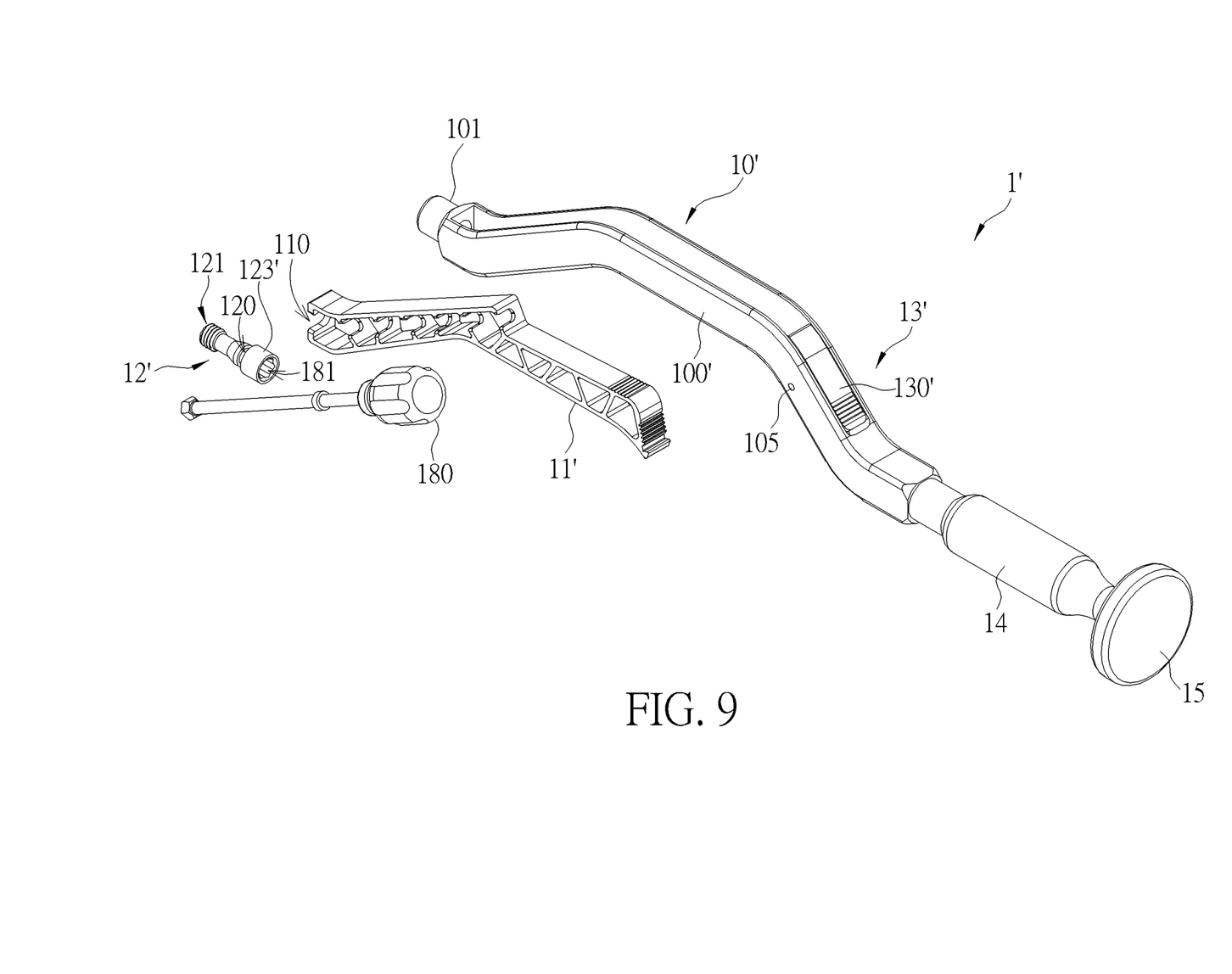
FIG. 9 is an exploded diagram of the surgical inserter according to the second embodiment.
Figure 10:
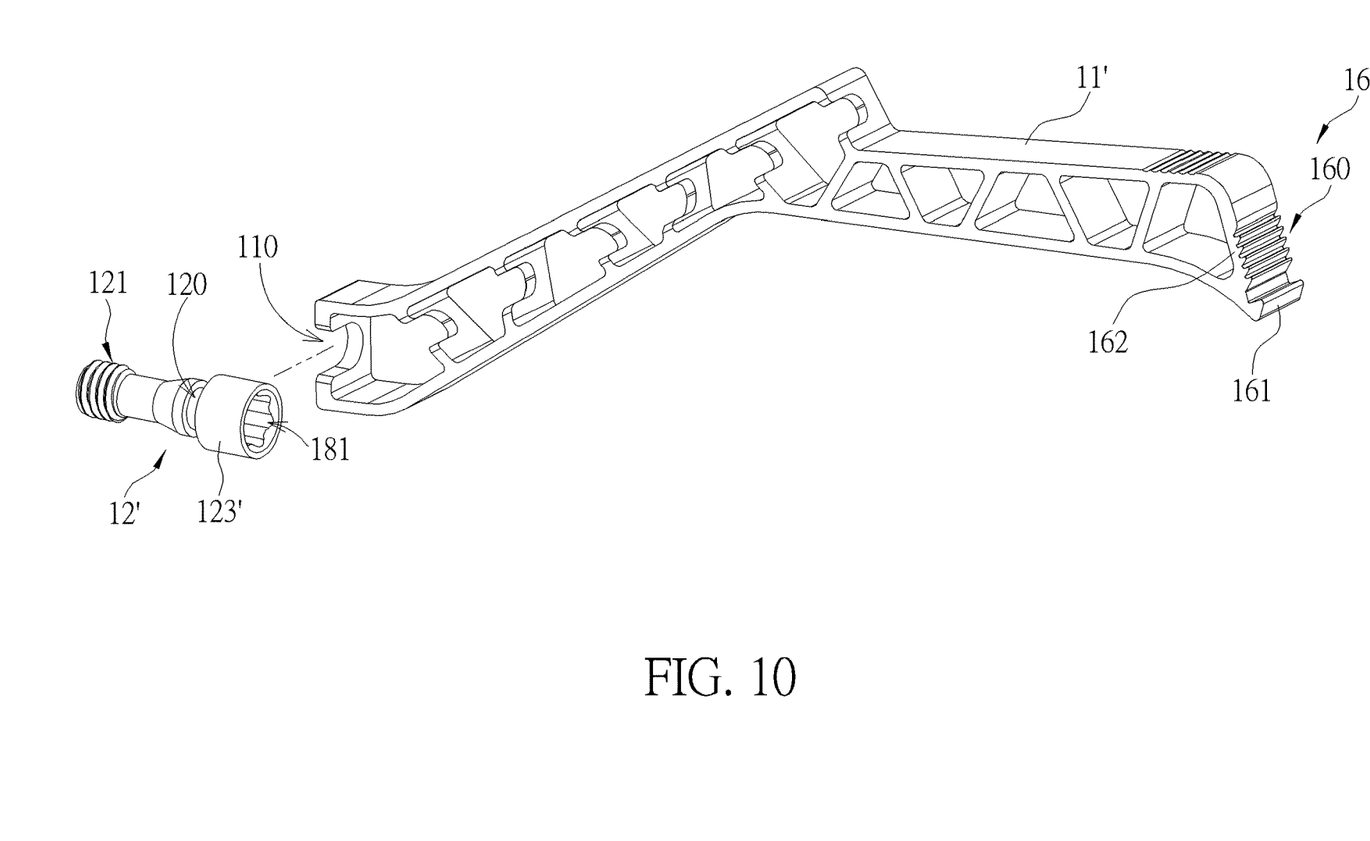
FIG. 10 is a diagram of a bolt and a lever according to the second embodiment.
Figure 11:
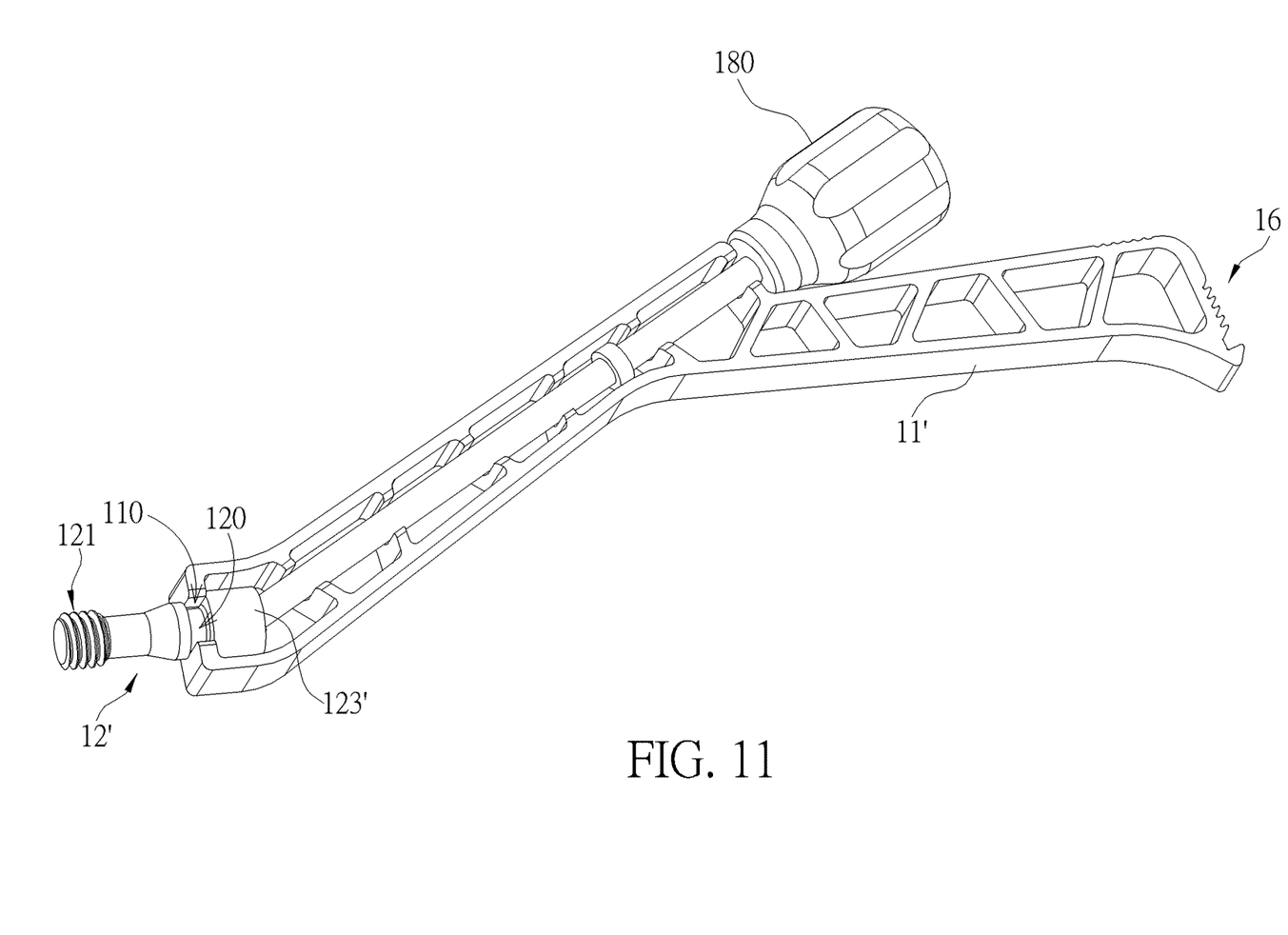
FIG. 11 is another diagram of the bolt, the lever, and a screw driver according to the second embodiment.

Please refer to FIGS. 5 to 7. The shaft 10 further includes two pins 103 disposed on the other end of shaft body 100. Two slots 132 are disposed on locking body 130 correspondingly. The two pins 103 pass through two slots 132 respectively, so that locking mechanism 13 is slidable relative to shaft body 100 by cooperation of two pins 103 and two slots 132. However, the sliding configuration is not limited to this embodiment.

Besides, the inserter 1 further includes a resilient component 17 disposed between locking mechanism 13 and shaft body 100 for resiliently recovering locking mechanism 13 to engage first ratchet 16. An avoiding section 104 is formed on another side of the shaft body 100 opposite to slot 102 for preventing interference between lever 11 and shaft body 100.

When it is desired to connect device 2 and inserter 1, the locking body 130 is operated to slide relative to shaft body 100 for disengaging second ratchet 131 from first ratchet 16. The angular movement of lever 11 relative to shaft body 100 is released, so that lever 11 can be adjusted to an unlocking position. Afterward, the resilient component 17 drives locking body 130 to recover when the locking body is released, so that second ratchet 131 engages with first engaging hook 161 for positioning lever 11 at the unlocking position (FIG. 5). At this moment, the device 2 can be connected to inserter 1 via connecting portion 121 of bolt 12, such as pre-screwing connecting portion 121 into a threaded hole on device 2.

After the device 2 is connected to inserter 1, the lever 11 can be operated to be bending relative to shaft body 100 from the unlocking position (FIG. 5), to a locking position (FIG. 6). During a period that lever 11 is bending relative to shaft body 100, the end of lever 11 pries bolt 12 gradually, so that device 2 is driven by bolt 12 to abut against an outer side of engaging head 101 tightly. In the meantime, the locking body 130 can be operated to drive second ratchet 131 to disengage from first engaging hook 161 to engage with some of first teeth 160 for positioning lever 11 at the locking position. Therefore, it ensures device 2 to tightly abut against the outer side of engaging head 101 all the time. However, in another embodiment, the lever 11 also can be positioned at another locking position between the locking position (FIG. 6), and the unlocking position (FIG. 5) by engaging second ratchet 131 with another some of first teeth 160.

When it is desired to loosen device 2 from inserter 1, the locking body 130 is operated to slide relative to shaft body 100, so that second ratchet 131 disengages from first teeth 160 to release the angular movement of lever 11 relative to shaft body 100. At this moment, the bending lever 11 recovers from the locking position (FIG. 6), and toward the unlocking position (FIG. 5), so that the first engaging hook 161 contacts with second ratchet 131. When the locking body 130 is released, the resilient component 17 drives locking body 130 to engage second ratchet 131 with first engaging hook 161. When the lever 11 is located at the unlocking position, the lever 11 does not pry bolt 12 anymore, so that the device 2 is loosened from inserter 1.

Furthermore, when it is desired to detach lever 11 from shaft body 100 for easy cleaning and sterilization, the locking body 130 is operated to slide relative to the shaft body 100, so that second ratchet 131 disengages from first ratchet 16 completely. At this moment, the lever 11 is located at a disassembling position (FIG. 7). Therefore, lever 11 and bolt 12 can be removed from slot 102 easily.

It should be noticed that since the height of each first tooth 160 is less than the height of first engaging hook 161, when the locking body 130 slides to disengage second ratchet 131 from first teeth 160 by a predetermined distance, the second ratchet 131 can contact with first engaging hook 161 for stopping lever 11 from jumping into the disassembling position suddenly. In other words, such design provides two-stage operation for preventing disengagement of lever 11 and shaft body 100 unintentionally, which improves convenience of operation.

Please refer to FIGS. 8 to 11. For simplicity, elements that have the same structures and functions as that illustrated in the aforementioned embodiment are provided with the same item numbers in this embodiment. The difference between the inserter 1 of the first embodiment and an inserter 1' of the second embodiment is described as follows. In this embodiment, a shaft body 100' is formed in a curved shape. A locking body 130' of a locking mechanism 13' is rotatably connected to shaft body 100' for selectively locking or releasing angular movement of a lever 11' relative to shaft body 100'. The shaft 10' further includes a pivotal pin 105 disposed on the other end of shaft body 100', and locking body 130' is pivoted to shaft body 100' by pin 105. The inserter 1' further includes a screw driver 180 for driving a bolt 12' to rotate. A socket 124 is formed on a head 123' of bolt 12' for engaging with screw driver 180. However, in another embodiment, the bolt 12' also can be driven by cooperation of bevel gears or other rotation transfer mechanisms.

Figure 12:
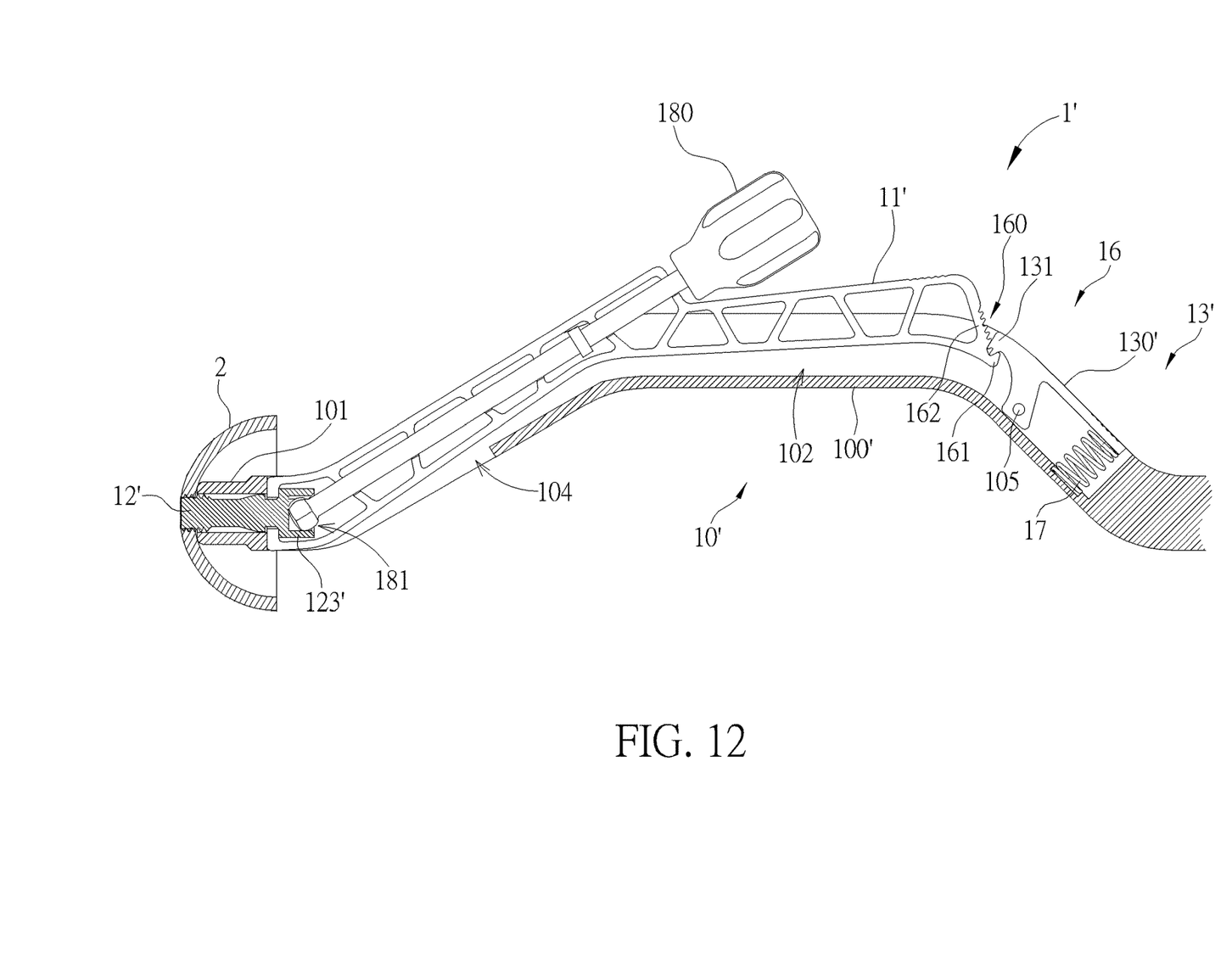
FIG. 12 is a diagram of the surgical inserter at an unlocking status according to the second embodiment.
Figure 13:
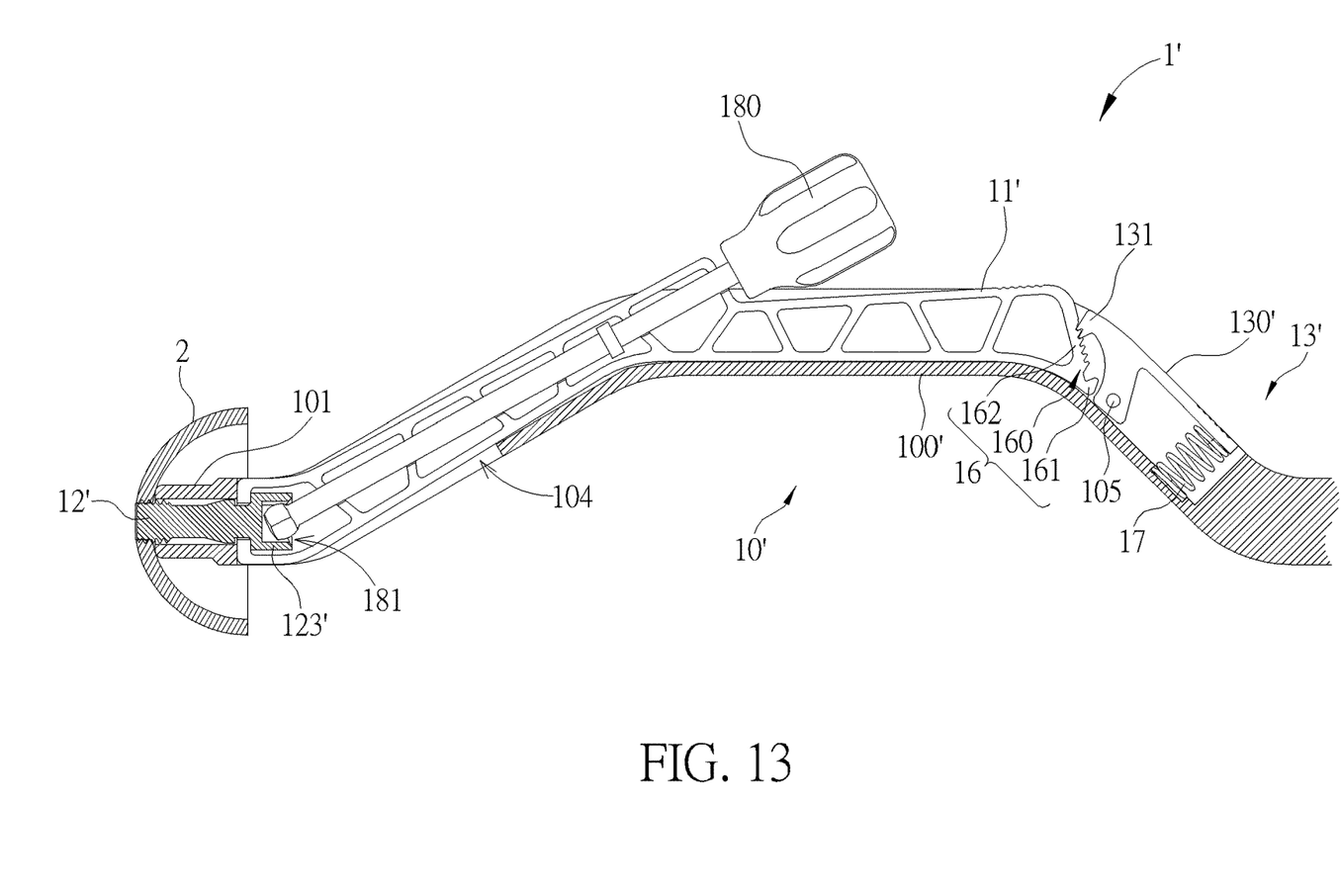
FIG. 13 is a diagram of the surgical inserter at a locking status according to the second embodiment.
Figure 14:
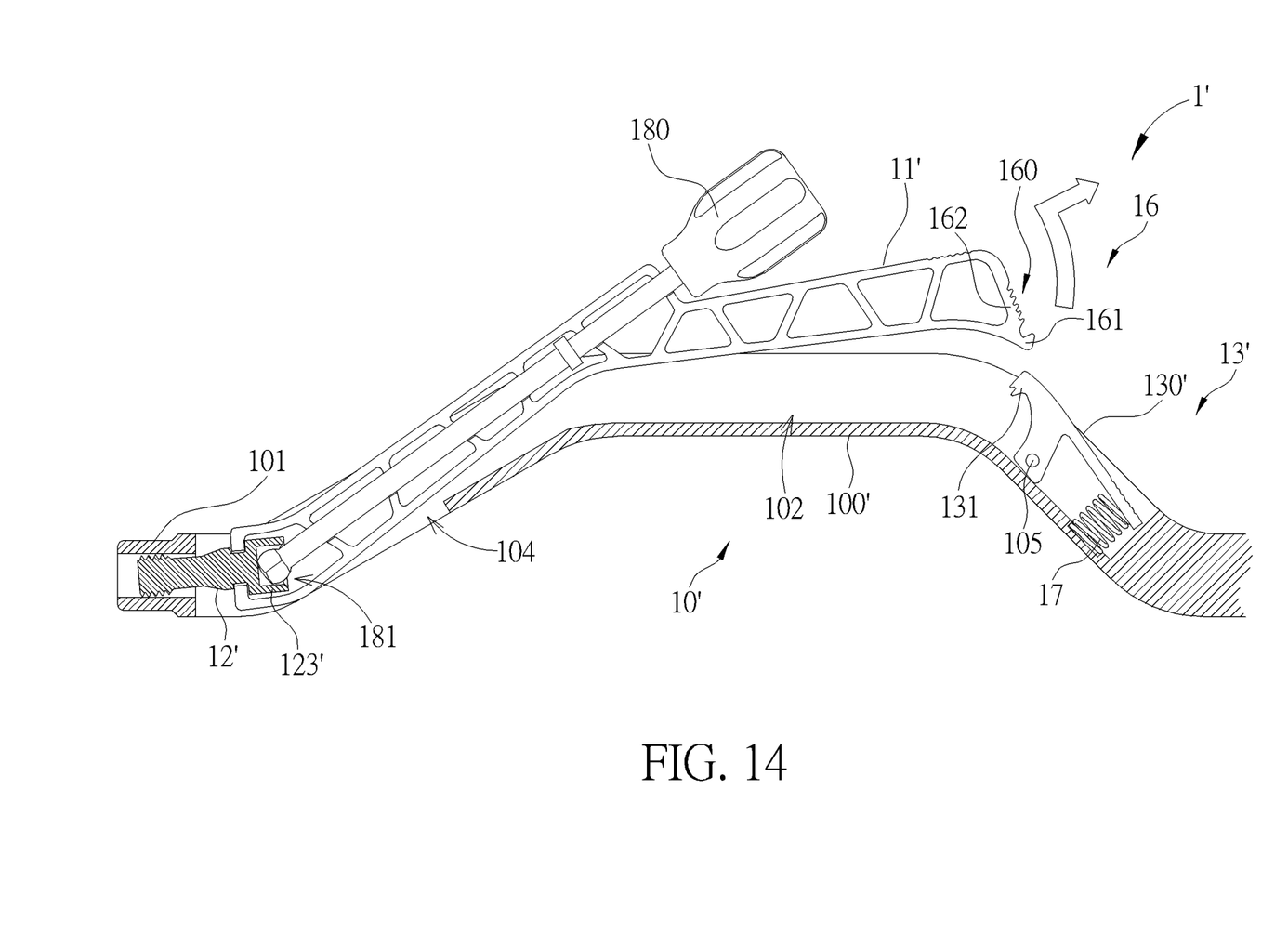
FIG. 14 is a diagram of the surgical inserter at a disassembling status according to the second embodiment.

Please refer to FIGS. 12 to 14. When it is desired to connect device 2 to inserter 1', the locking body 130' is operated to rotate relative to shaft body 100' for releasing angular movement of lever 11' relative to shaft body 100', so that lever 11' can be operated to be located at an unlocking position (FIG. 12). Therefore, the device 2 can be connected to inserter 1' by cooperation of screw driver 180 and bolt 12'.

After the device 2 is connected to inserter 1', the lever 11' is operated to be bending relative to shaft body 100' from the unlocking position (FIG. 12), to a locking position (FIG. 13). During a period that lever 11' is bending relative to shaft body 100', an end of lever 11' pries bolt 12' gradually, so that device 2 is driven by bolt 12' to abut against the outer side of engaging head 101 tightly. In the meantime, the locking body 130' can be operated to rotatably drive second ratchet 131 to disengage from first engaging hook 161 so as to engage with some of first teeth 160 for positioning lever 11' at the locking position manually. Therefore, it ensures the device 2 to tightly abut against the outer side of engaging head 101 all the time.

When it is desired to loosen device 2 from inserter 1', the locking body 130' is operated to rotate relative to shaft body 100', so that second ratchet 131 disengages from first teeth 160 to release the angular movement of lever 11' relative to shaft body 100'. At this moment, the bending lever 11' recovers from the locking position (FIG. 13), and toward the unlocking position (FIG. 12), so that first engaging hook 161 contacts with second ratchet 131. When the locking body 130' is released, the resilient component 17 drives locking body 130' to recover for engaging second ratchet 131 with first engaging hook 161. When the lever 11' is located at the unlocking position, the lever 11' does not pry bolt 12' anymore, so that the device 2 is loosened from inserter 1'.

Furthermore, when it is desired to detach lever 11' from shaft body 100' for easy cleaning and sterilization, the locking body 130' is operated to rotate relative to shaft body 100', so that second ratchet 131 disengages from first ratchet 16 completely. At this moment, the lever 11' is located at the disassembling position (FIG. 14). Therefore, lever 11', bolt 12', and screw driver 180 can be removed from slot 102 easily. Therefore, it is easy to clean and sterilize the inserter 1' thoroughly.

In contrast to the prior art, the present embodiment utilizes the lever for prying the bolt to drive the medical device to abut against the outer side of the engaging head tightly. The present embodiment further utilizes the locking mechanism for locking the angular movement of the lever relative to the shaft body, so as to ensure the medical device to abut against the engaging head all the times. Therefore, the present embodiment prevents loose movement of the medical device relative to the surgical inserter during a surgical operation, which enhances precision of surgical operation. Besides, structure of the surgical inserter of the present embodiment is simpler than conventional designs, and can be disassembled easily, so that it is easy for users to clean and sterilize the surgical inserter thoroughly, which substantially reduces a risk of infection.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. A surgical inserter for a medical device, the surgical inserter comprising:
a shaft comprising a shaft body and an engaging head disposed on a distal end of the shaft body;
a lever angularly movably disposed in the shaft body, a distal end of the lever being adjacent to an inner side of the engaging head;
a bolt mounted on the distal end of the lever and passing through the engaging head, the bolt being configured to connect the medical device; and
a locking mechanism slidably or pivotally movably disposed on a proximal end of the shaft body, the locking mechanism configured to selectively lock or release angular movement of the lever relative to the shaft body;
wherein when the lever is being bent by angularly moving the lever relative to the shaft body, the distal end of the lever pries the bolt, so that the medical device is driven by the bolt to abut against an outer side of the engaging head tightly; and
wherein the surgical inserter further comprises a first ratchet disposed on a proximal end of the lever opposite to the distal end of the lever, the locking mechanism comprising a locking body and a second ratchet disposed on a side of the locking body corresponding to the first ratchet, and the first ratchet engaging with the second ratchet for locking the angular movement of the lever relative to the shaft body.

2. The surgical inserter of claim 1, wherein the first ratchet comprises a plurality of first teeth, a first engaging hook, and a first ratchet body, the plurality of first teeth and the first engaging hook protrude from the first ratchet body, the first engaging hook is located at a side of the plurality of first teeth, a height of each the plurality of first teeth is less than a height of the first engaging hook, and the second ratchet selectively engages with some of the plurality of first teeth or the first engaging hook for locking the angular movement of the lever relative to the shaft body.

3. The surgical inserter of claim 2, wherein the lever is located at a locking position when the second ratchet engages with some of the plurality of first teeth, the lever is located at an unlocking position when the second ratchet engages with the first engaging hook, and the lever is located at a disassembling position when the second ratchet disengages from the first ratchet.

4. The surgical inserter of claim 1, wherein each of the shaft body and the lever is formed in a straight shape, and a head of the bolt is configured to be received in the lever and rotated along with the shaft body and the lever.

5. The surgical inserter of claim 1, wherein the locking body is slidably connected to the shaft body for selectively locking or releasing the angular movement of the lever relative to the shaft body.

6. The surgical inserter of claim 5, wherein the shaft further comprises at least one pin disposed on the proximal end of the shaft body, at least one slot is disposed on the locking body and located at a position corresponding to the at least one pin.

7. The surgical inserter of claim 1, wherein the shaft body is formed in a curved shape, and the surgical inserter further comprises a screw driver for driving the bolt to rotate.

8. The surgical inserter of claim 7, wherein a socket is formed on a head of the bolt for engaging with the screw driver, so that the screw driver drives the bolt to rotate.

9. The surgical inserter of claim 1, wherein the locking body is pivotally connected to the shaft body for selectively locking or releasing the angular movement of the lever relative to the shaft body.

10. The surgical inserter of claim 9, wherein the shaft further comprises a pivotal pin disposed on the proximal end of the shaft body, and the locking body is pivotally connected to the shaft body by the pivotal pin.

11. The surgical inserter of claim 1, wherein the lever is detachably disposed on the shaft body.

12. The surgical inserter of claim 1, further comprising a resilient component disposed between the locking mechanism and the shaft body for resiliently recovering the locking mechanism.

13. The surgical inserter of claim 1, wherein a notch is formed on the distal end of the lever near the engaging head, and the bolt comprises a neck portion engaged with the notch on the lever.

14. The surgical inserter of claim 1, wherein the bolt comprises a connecting portion for connecting the medical device by a threaded connection, a bayonet connection, or a dovetail connection.

15. The surgical inserter of claim 1, further comprising:
a handle portion extending from the proximal end of the shaft body; and
an impaction plate connected to the handle portion for receiving an external force.

16. The surgical inserter of claim 1, wherein an accommodating slot is formed on a side of the shaft body for receiving the lever and the locking mechanism.

17. The surgical inserter of claim 16, wherein an avoiding section is formed on another side of the shaft body opposite to the accommodating slot for preventing interference between the lever and the shaft body.

18. The surgical inserter of claim 1, wherein the surgical inserter is an acetabular cup inserter, and the medical device is an acetabular cup implant.

19. The surgical inserter of claim 1, wherein the medical device is a prosthetic implant, a provisional implant or an instrument.

* * * * *